United States Patent
Osborne

(10) Patent No.: US 8,123,769 B2
(45) Date of Patent: Feb. 28, 2012

(54) THROMBUS REMOVAL DEVICE

(75) Inventor: Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 352 days.

(21) Appl. No.: 11/502,659

(22) Filed: Aug. 11, 2006

(65) Prior Publication Data

US 2007/0038225 A1 Feb. 15, 2007

Related U.S. Application Data

(60) Provisional application No. 60/707,638, filed on Aug. 12, 2005.

(51) Int. Cl.
 *A61B 17/22* (2006.01)
(52) U.S. Cl. ........................................ 606/159
(58) Field of Classification Search ............... 606/127, 606/159, 200, 110, 113, 114, 128
See application file for complete search history.

(56) References Cited

U.S. PATENT DOCUMENTS

| | | |
|---|---|---|
| 3,683,891 A | 8/1972 | Eskridge et al. |
| 3,749,085 A | 7/1973 | Willson et al. |
| 4,030,503 A | 6/1977 | Clark, III |
| 4,706,671 A | 11/1987 | Weinrib |
| 4,886,490 A | 12/1989 | Shiber |
| 5,011,488 A | 4/1991 | Ginsburg |
| 5,192,268 A | 3/1993 | Shiber |
| 5,269,751 A | 12/1993 | Kaliman et al. |
| 5,284,486 A | 2/1994 | Kotula et al. |
| 5,895,398 A | 4/1999 | Wensel et al. |
| 6,063,069 A | 5/2000 | Cragg et al. |
| 6,066,158 A | 5/2000 | Engelson et al. |
| 6,436,112 B2 | 8/2002 | Wensel et al. |
| 6,454,775 B1 | 9/2002 | Demarais et al. |
| 6,485,497 B2 | 11/2002 | Wensel et al. |
| 6,530,935 B2 | 3/2003 | Wensel et al. |
| 6,663,650 B2 | 12/2003 | Sepetka et al. |
| 6,692,508 B2 | 2/2004 | Wensel et al. |
| 6,692,509 B2 | 2/2004 | Wensel et al. |
| 6,730,104 B1 | 5/2004 | Sepetka et al. |
| 2006/0074409 A1* | 4/2006 | Schuermann ............... 606/2.5 |

* cited by examiner

*Primary Examiner* — Ryan Severson
*Assistant Examiner* — David Eastwood
(74) *Attorney, Agent, or Firm* — Brinks Hofer Gilson & Lione

(57) ABSTRACT

A thrombi removal device includes a shaft with a distal end and a proximal end and a helical coil attached at one end to the distal end of the shaft and extending in the distal direction from the shaft. The coil has a plurality of body portions with turns or winding spaced apart longitudinally and laterally to facilitate screwing the coil into the thrombus and to provide a sufficient open area into which the thrombus can be captured. The distal end of the coil is provided with a loop. The angle of the loop relative to a longitudinal axis extending through the helical coil is about the same as the angle of at least one body portion.

20 Claims, 6 Drawing Sheets

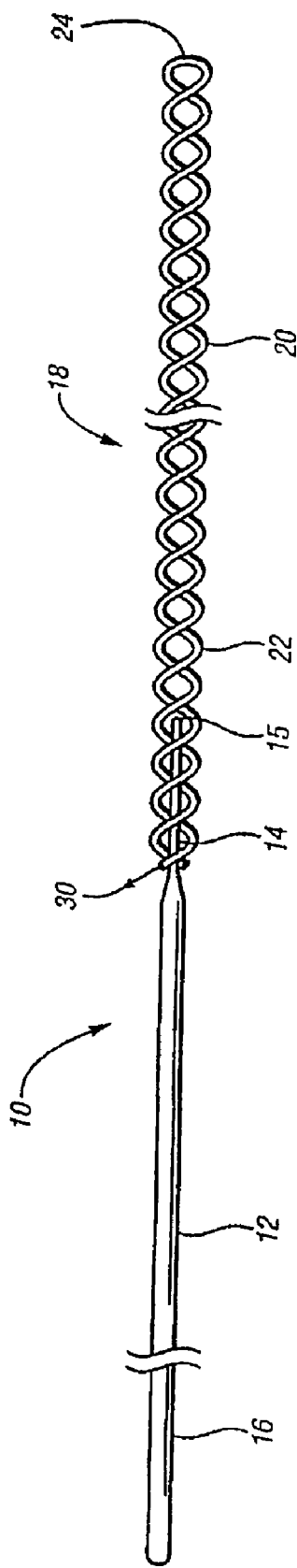
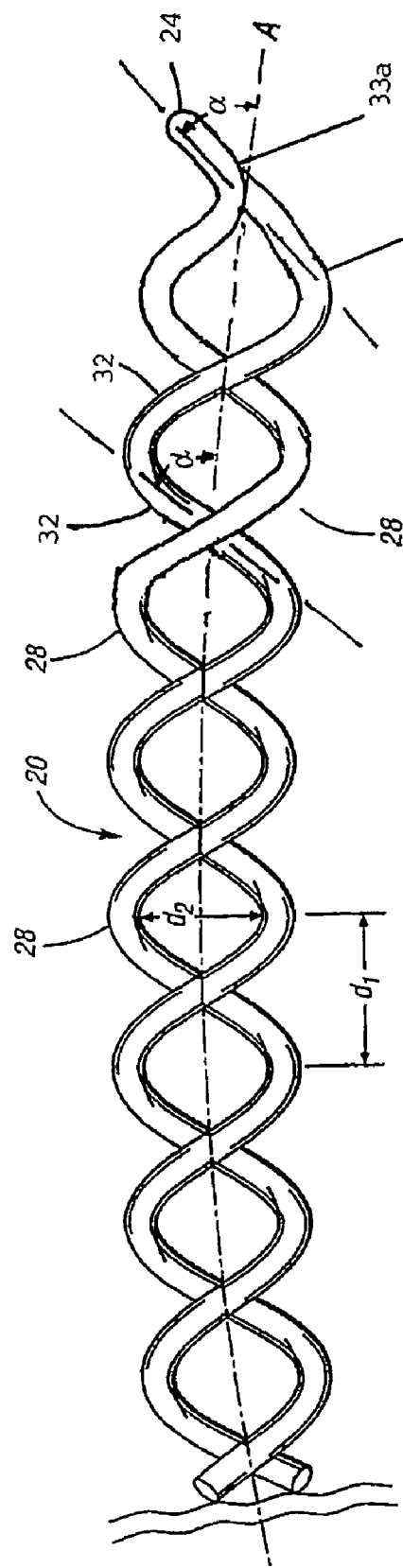
Fig. 1a
Fig. 1b

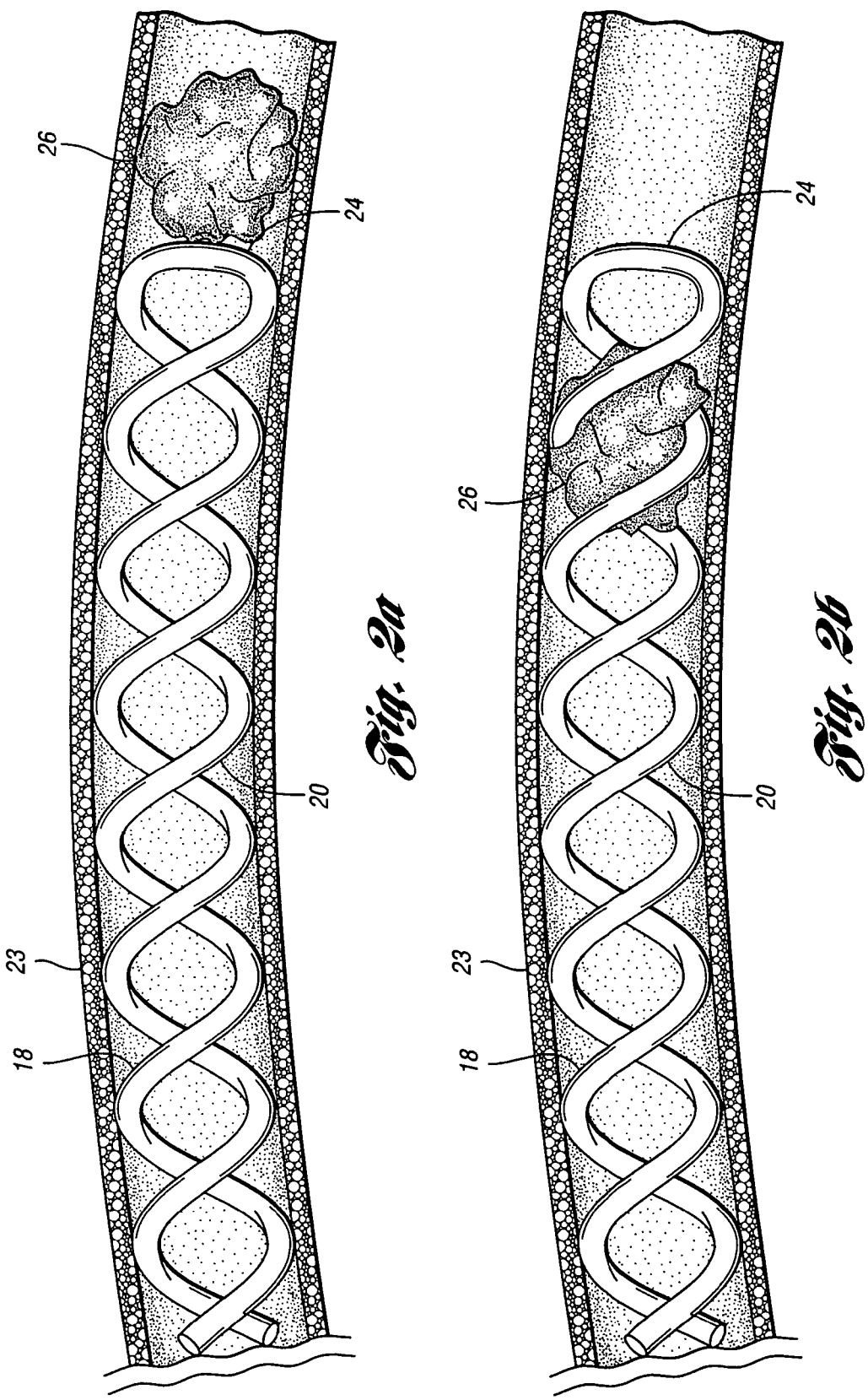

THROMBUS REMOVAL DEVICE

CROSS-REFERENCE TO RELATED APPLICATIONS

This application claims the benefit of U.S. Provisional Application No. 60/707,638, filed on Aug. 12, 2005, entitled "THROMBUS REMOVAL DEVICE," the entire contents of which are incorporated herein by reference.

BACKGROUND

The present invention relates to medical devices. Specifically, the invention relates to a device for removing blood clots or thrombus from body vessels, such as small arteries associated with the brain.

Mechanical thrombectomy is a procedure that has been in widespread use for many years. Typical thrombectomy devices are balloons that are inflated in a vessel, then withdrawn to pull clots into a sheath which can be withdrawn from the patient to remove the clots. Other devices are simple open ended catheters into which a clot is aspirated and removed from the patient. Another thrombectomy device employs a basket device that is opened within the clot so that the clot becomes captured in the basket, which can be retrieved along with the clot. Still other devices use a small corkscrew shaped device that is collapsed inside a catheter, passed through the clot, pushed out of a delivery sheath allowing the device to expand, then retracted, capturing the clot for removal. Some corkscrew devices are simply "screwed" into the clot, then retracted into a catheter for removal.

All of these devices may, however, have certain disadvantages. For example, the balloon catheter devices are first advanced through the clot before they can be inflated and retracted. The process of penetrating the clot with the balloon catheter device tends to push the clot deeper into the arterial circulation where it becomes even more difficult to remove. This issue also occurs with basket and corkscrew devices that are collapsed into an outer delivery sheath and passed through the clot before they can be deployed and retracted. The action of pushing a device through the center of the clot pushes the clot deeper into the artery and sometimes fragments the clot, making it even more dangerous as an embolus. The corkscrew devices that are screwed into the clot usually have a smooth rounded tip to prevent the corkscrew from penetrating the vessel wall or otherwise damaging the vessel wall as it is screwed into the clot. With these devices, however, the smooth, rounded central tip does not screw into the clot, but instead is pushed into the clot and then the remainder of the corkscrew is screwed into the clot. This results in a pushing force on the center of the clot and a pulling force on the periphery of the clot. These counter forces tend to macerate or fragment the clot and result in only a small part of the clot being captured. The small corkscrew devices with sharp tips can screw directly into the clot; however, they can penetrate the vessel wall just as easily as they can penetrate and capture the clot. As a result, the use of such devices is very risky and thus seldom performed. If a bead or ball is applied to the tip of the device that is large enough to protect the vessel wall, it will be so large that it will tend to push the clot distally, deeper into the artery rather than penetrate the clot such that the clot can be captured and removed.

Another issue associated with conventional thrombectomy devices is that they are typically too large and too stiff for use in the small tortuous vessels in the brain. Some of the conventional devices also use a central mandrel wire or some other structure for support, which displace clots, making it difficult to capture all the clot material.

SUMMARY

The present invention provides a thrombi removal device that is small and flexible for use, for example, in the vasculature of the brain to capture clots in the vasculature. The distal tip of the device is configured as a loop to eliminate the danger of inadvertently boring through an artery wall while attempting to capture the clot.

In general, the device includes a shaft with a distal end and a proximal end and a helical coil attached at one end to the distal end of the shaft and extending in the distal direction from the shaft. The coil has a plurality of body portions with turns spaced apart longitudinally and laterally to facilitate screwing the coil into the thrombus and to provide a sufficient open area into which the thrombus can be captured. The distal end of the coil is provided with a loop. The angle of the loop relative to a longitudinal axis extending through the helical coil is about the same as the angle of at least one body portion.

Further features and advantages will be apparent from the following description and from the claims.

BRIEF DESCRIPTION OF THE DRAWINGS

FIG. 1a is a perspective view of a thrombi removal device in accordance with one embodiment of the present invention;

FIG. 1b is a close-up side view of a distal portion of the thrombi removal device of FIG. 1a;

FIG. 2a is a close-up view of the distal portion of the thrombi removal device as it engages a thrombus;

FIG. 2b is a close-up view of the distal portion of the thrombi removal device after disposing into the thrombus;

FIG. 3b is an exploded view of the assembly of FIG. 3a;

DETAILED DESCRIPTION

Figure 1C:
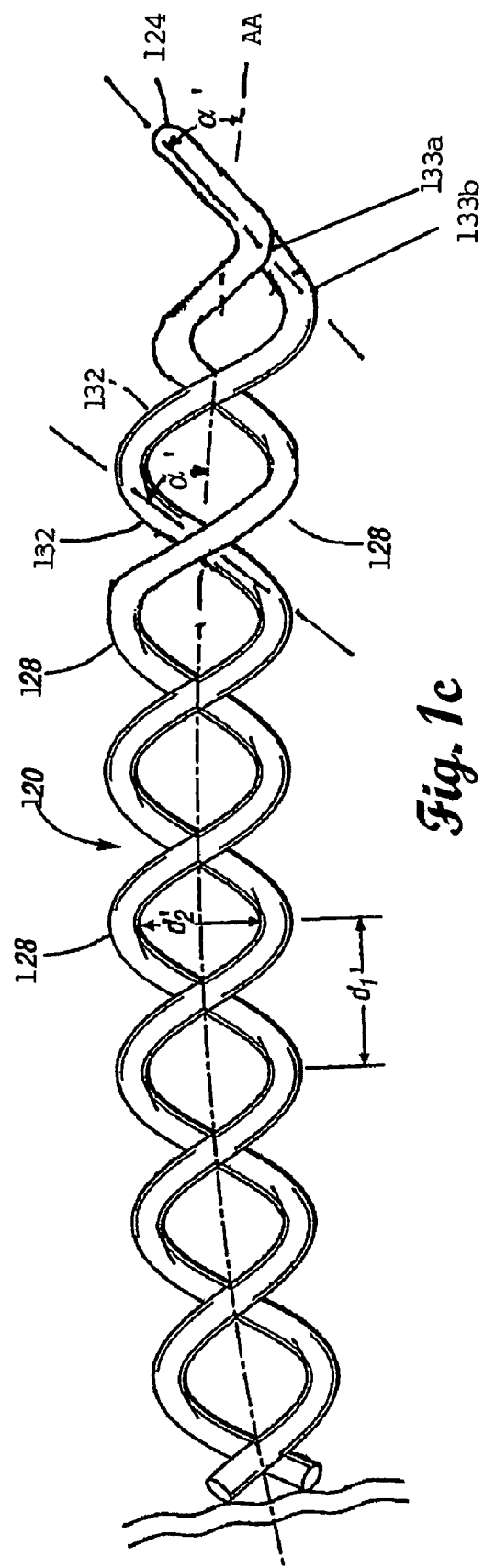
FIG. 1c is an alternative example of the distal portion of FIG. 1b.

Referring now to FIGS. 1a and 1b, a thrombi removal device embodying the principles of the present invention is illustrated therein and designated at 10. As its primary components, the device 10 includes a shaft 12 with a distal end 14 and a proximal end 16 and a helical coil 18 with a distal portion 20 and a proximal portion 22. The device 10 is small and flexible to enable the helical coil 18 to penetrate thrombi or clots without posing a danger of penetration to a body vessel wall.

Figure 2C:
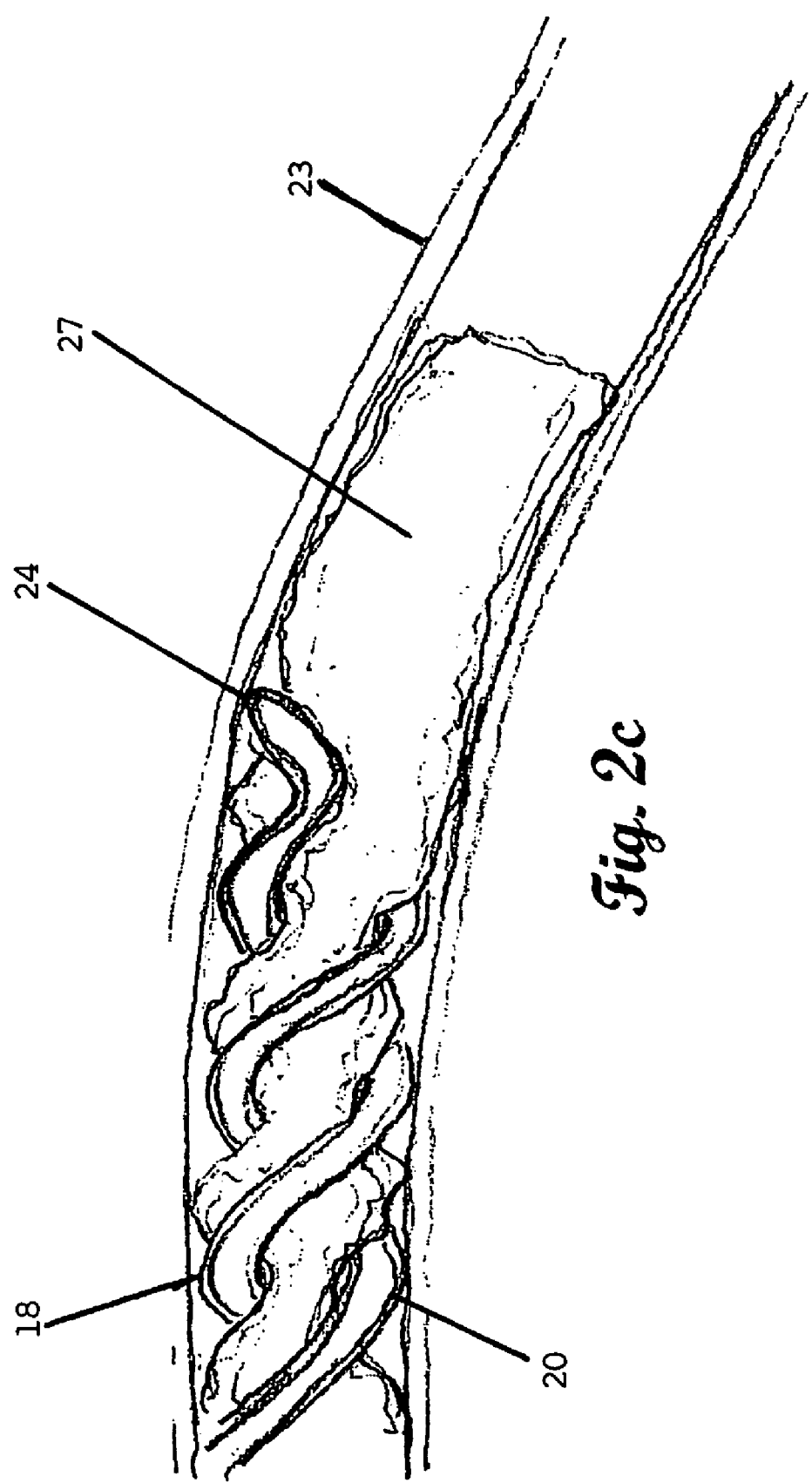
FIG. 2c is a close-up view of the distal portion of the thrombi removal device after disposing into a long thrombus.

Referring also to FIGS. 2a and 2b, the device 10 operates as a torqueable wire guide through a body vessel 23. Specifically, the tip 24 of the helical coil 18 is positioned within closed proximity of a thrombus or clot 26, and then the physician rotates the shaft 12 so that the helical coil 18 screws into the clot 26. As best shown in FIG. 2b, after the helical coil 18 has sufficiently screwed into the clot 26 to capture the clot 26 in the distal portion 20 of the helical coil 18, the helical coil 18 and the clot 26 are removed by retracting the coil and clot into a catheter as the physician pulls on the shaft 12. In addition, the device 10 is capable of removing clots of differing lengths, for example, a long clot 27 as shown in FIG. 2c. In this embodiment, this is accomplished by the helical coil 18 being longer than the long clot 27. As a result, the device 10 may capture either the shorter clot 26 (see FIG. 2b) or the long clot 27 (see FIG. 2c). As a result, the device 10 has features that make it well suited for very small vessels that are encountered in the brain. Furthermore, the device 10 is configured to be manufactured easily.

In certain implementations, the helical coil 18 is made from a wire with a diameter of about 0.004 inch. The wire can be made from any suitable material, such as stainless steel, platinum, Nitinol, MP35N, and palladium. The wire is initially coiled into a helical spring (with a diameter of about 0.018 inch) that is folded or doubled back on itself and then twisted together into a two-filar helical coil with a plurality of body portions 32, as shown, in FIG. 1b.

The longitudinal and lateral spacing, $d_1$ and $d_2$, between the individual winds or turns 28 of the coil are selected so that the helical coil 18 screws into the clot and to provide ample open area for secure clot capture. The proximal end of the helical coil terminates with two ends 30 and the portion of the coil near the tip 24 is shaped as a small loop formed when the coil is folded or bent through about 180°. The overall diameter of the two-filar helical coil 18 is about the same size as the unfolded spring, that is, approximately 0.018 inch. In some implementations, the length of the helical coil 18 is in the range between about 2 and 10 cm. In a particular implementation, the coil 18 is about 5 cm long. The loop at the tip 24 is a single loop with an angle ($\alpha$) relative to a longitudinal axis (A) that is the same or about the same as the angle of a body portion 32 that extends away from the loop as it extends from the bottom to the top of the distal portion 20 illustrated in FIG. 1b.

When the loop is formed at the tip 24, an adjacent first bend 33a and a second bend 33b are also formed. In one embodiment, the first bend 33a may be aligned approximately with or be formed tangent to the longitudinal axis (A) as shown in FIG. 1b. As shown, the first bend 33a has a turn or bend that is tangent or in alignment with axis (A). An alternative embodiment shown in FIG. 1c includes features equivalent to FIG. 1b, for example, a helical coil 118 is equivalent to the helical coil 18, a body portion 132 is equivalent to the body portion 32, and a longitudinal axis (AA) is equivalent to the longitudinal axis (A). However, in the embodiment of FIG. 1c a first bend 133a may be configured in non-alignment relative to the longitudinal axis (AA). As shown, the first bend 133a has a turn or bend that is not tangent or in alignment with axis (A). In yet another example, the first bend may be aligned with the second bend. Accordingly, the loop screws into the clot without applying a pushing force parallel to the longitudinal axis of the vessel 23 so that the clot is not pushed in the distal direction. Hence, the configuration of the loop protects the vessel wall by not enabling the helical coil 18 to corkscrew and penetrate into the vessel wall, but enables the helical coil to corkscrew and penetrate into the clot to capture the clot.

The distal loop at the tip 24 can be filled with a highly radiopaque material, such as gold, to make the tip or leading end of the helical coil 18 visible under fluoroscopy. The helical coil 18 itself can be made of platinum wire for added radiopacity. Rather than using a wire, the helical coil 18 can be laser cut from a tube, and then the loop at the tip is bent into the correct angle and position.

The shaft is preferably made of a material that transmits rotation or torque around curves in the vasculature. That is the shaft 12 functions similar to a speedometer cable. Shape memory alloys are well suited to this application because they have the desirable property of becoming rigid when heated above a transition temperature. A shape memory alloy suitable for the present invention is Ni—Ti available under the more commonly known name Nitinol. When this material is heated above the transition temperature, the material undergoes a phase transformation from martensite to austenite, such that the material becomes rigid. The transition temperature is dependent on the relative proportions of the alloying elements Ni and Ti and the optional inclusion of alloying additives, as is selected so the material is austenite at body temperature.

The proximal end of the helical coil 18 is attached to the distal end 14 of the shaft 12 with suitable attachment means, such as glue or solder. The distal end 14 of the shaft 12 preferably tapers to a tip 15 so that there is a gradual transition from the stiff portion of the shaft 12 to the helical coil 18. The tapered portion can be any length and the decreasing diameters of the tapered portion can be any suitable combination. In some implementations, the shaft is made of Nitinol wire with a diameter of about 0.014 inch and is about 145 cm long. The distal end 14 tapers from a diameter of about 0.014 inch to about 0.003 inch at the tip 15 over a length of about 15 cm. The shaft 12 may be provided with a pin vise or any other suitable handle device to facilitate rotation of the shaft 12 and hence the helical coil 18.

Although these dimensions and this description relate to a device sized to work in the cerebral arteries, the device can be dimensioned to work in any size artery or anatomy for thrombectomy, embolectomy or crossing completely stenosed or nearly completely stenosed areas within body vessels.

Figure 3A:
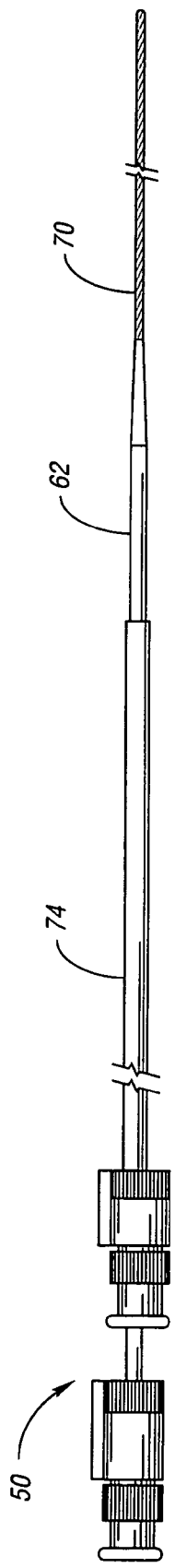
FIG. 3a is a side view of an assembly for deploying and retrieving the thrombi removal device in accordance with one embodiment of the invention.
Figure 3B:
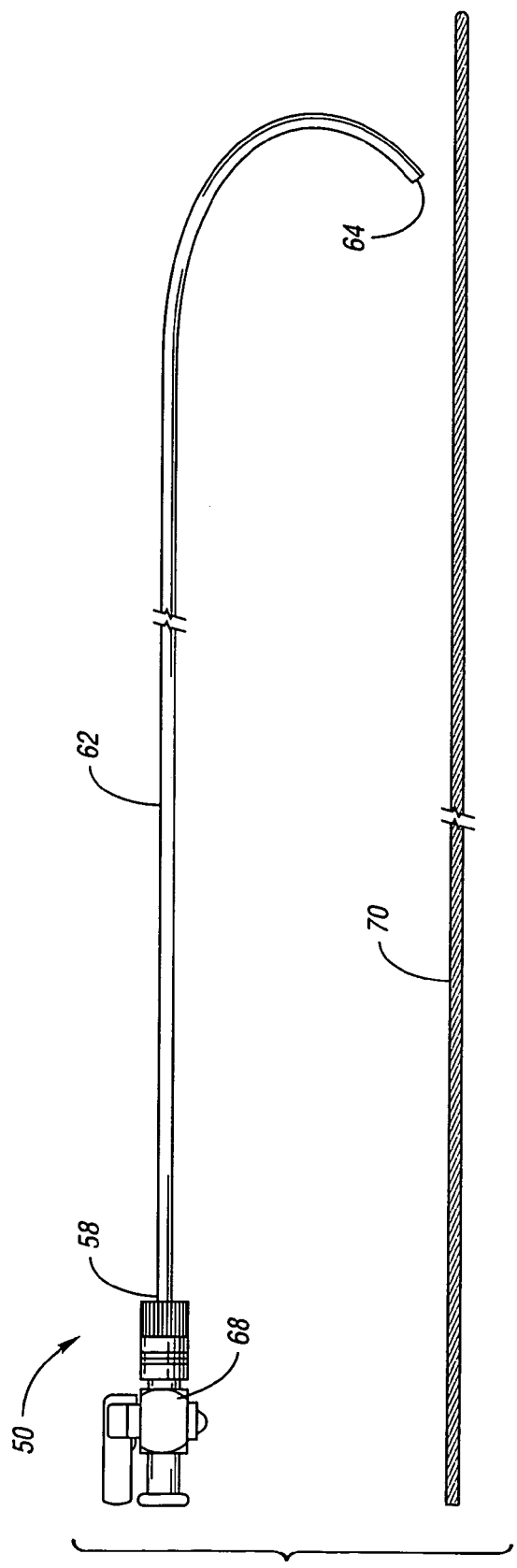

The thrombi removal device 10 may be used independently without any other delivery system or mechanism. Alternatively, the device 10 may be used, for example, with an assembly 50 as depicted in FIGS. 3a and 3b.

As shown, the assembly 50 includes an inner catheter 62 with a distal end 64 through which the device 10 is positioned for deployment in the body vessel. The inner catheter 62 is preferably made of a soft, flexible material such as silicon or any other suitable material. Generally, the inner catheter 62 also has a proximal end 58 and a plastic adaptor or hub 68 to receive the thrombi removal device 10. The size of the inner catheter 62 is based on the size of the body vessel into which the catheter 62 is inserted, and the size of the thrombi removal device 10.

The assembly 50 may also include a wire guide 70 configured to be percutaneously inserted within the vasculature to guide the inner catheter 62 to a location adjacent a thrombus. Alternatively, the thrombi removal device 10 may be employed as a wire guide.

In use, the device 10 is placed in the inner catheter 62 prior to treatment of the thrombus. The device is then guided through the inner catheter preferably from the hub 72 and distally beyond the distal end 64 of the inner catheter 62 to a location within the vasculature near the thrombus.

The assembly 50 may include a polytetrafluoroethylene (PTFE) introducer sheath 74 for percutaneously introducing the wire guide 70 and the inner catheter 62 in a body vessel. Of course, any other suitable material may be used for the sheath 74. The introducer sheath 74 may have any suitable size, e.g., between about three-french and eight-french. The introducer sheath 74 facilitates inserting the inner catheter 62 percutaneously to a desired location in the body vessel and provides stability to the inner catheter at a desired location in the body vessel. For example, as the introducer sheath 74 is held stationary within an artery, it adds stability to the inner catheter 62, as the inner catheter 62 is advanced through the introducer sheath 74 to a desired location in the vasculature.

When the distal end 64 of the inner catheter 62 is at a location near the thrombus, the thrombi removal device 10 is inserted through the inner catheter 62 and is advanced coaxially through the inner catheter 62 for deployment through the distal end 64 of the inner catheter. In this configuration, the proximal end 16 of the shaft 12 can be used to mechanically advance or push the thrombi removal device 10 through the catheter.

Figure 4:
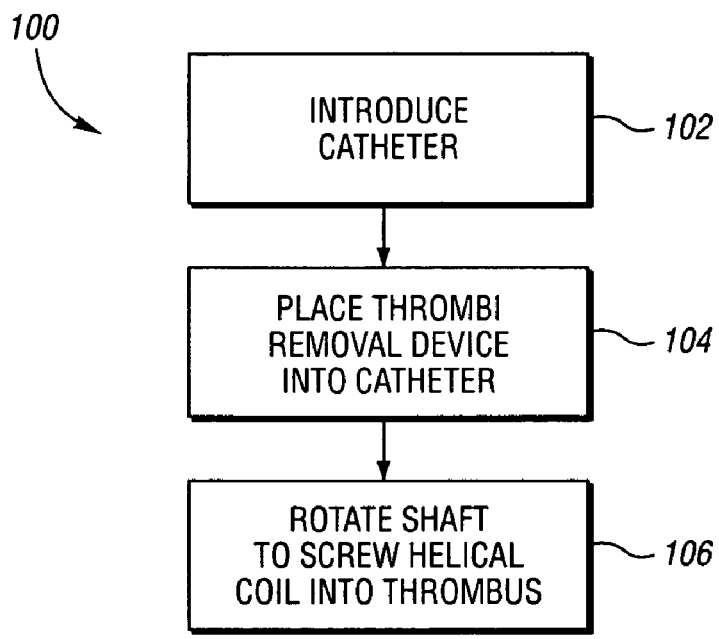
FIG. 4 is a flow chart of a sequence of steps for deploying a thrombi removal device in a body vessel.

Turning now to FIG. 4, there is shown a sequence of steps of a process 100 for removing thrombi in a body vessel when employing the assembly 50 and the thrombi removal device 10. In step 102, the process 100 includes percutaneously introducing the inner catheter 62 into a body vessel. The physician may use any suitable means, for example, fluoroscopy, to verify the placement of inner catheter 62.

Next, in step 104, the thrombi removal device 10 is placed in the inner catheter 62 and advanced beyond the distal end 64 of the inner catheter. Then, in step 106, the physician rotates the shaft 12 to screw the helical coil 18 into the thrombus until the thrombus is captured within the helical coil. After capturing the thrombus, the physician may advance the device 10 further in the distal direction toward additional thrombi that may reside in the vessel and then repeat the procedure to capture the additional thrombi.

Figure 5:
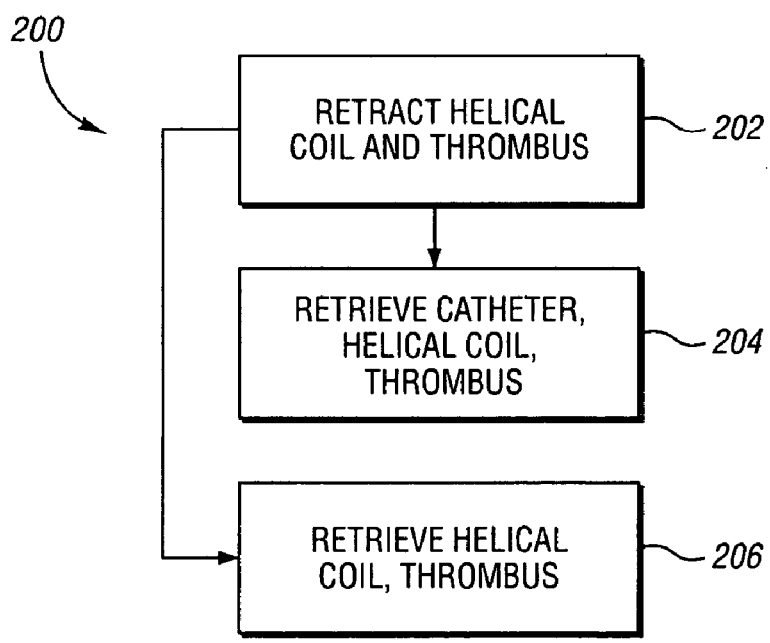
FIG. 5 is a flow chart of a sequence of steps for retrieving a thrombi removal device and a thrombus from a body vessel.

In yet another example of the present invention, FIG. 5 depicts a process 200 for retrieving the thrombi removal device after it has captured a thrombus or thrombi. In step 202, the physician pulls the shaft 12 to retract the helical coil 18 and the captured thrombus into the inner catheter 62.

Then, in step 204, the inner catheter 62 along with the thrombi removal device 10 and captured thrombi are retrieved from the body vessel. Alternatively, the inner catheter is not removed, but the thrombi removal device 10 and captured thrombi are retrieved from the patient's body by pulling the thrombi removal device out of the inner catheter 62, as indicated by optional step 206. As such, after the helical coil is cleansed of the thrombi, the device 10 can be reinserted into the inner catheter 62 to capture additional thrombi, or another device may be inserted into the inner catheter 62 to perform an alternative procedure.

As a person skilled in the art will readily appreciate, the above description is meant as an illustration of implementations of the principles of this invention. This description is not intended to limit the scope or application of this invention in that the invention is susceptible to modification, variation and change, without departing from the spirit of this invention, as defined in the following claims.

What is claimed is:

1. A thrombi removal device comprising:
a shaft including a distal end and a proximal end; and
a helical coil including a proximal end attached to the distal end of the shaft, a plurality of spaced apart body portions each having bends forming a helix, and a distal tip shaped as a loop, wherein first and second bends formed adjacent the loop orient the loop at an angle relative to a longitudinal axis extending through the helical coil, at least one body portion having an angle relative to the longitudinal axis that is substantially the same as the angle at which the loop is oriented, wherein the loop is oriented at an angle relative to the longitudinal axis such that the distal tip is spaced a distance from the longitudinal axis, the body portions having a substantially same diameter along an entire length of the helical coil.

2. The device of claim 1 wherein the shaft is made of shape memory alloy.

3. The device of claim 2 wherein the shape memory alloy is Nitinol.

4. The device of claim 1 wherein the shaft has a length of about 145 cm.

5. The device of claim 1 wherein the shaft has a diameter of about 0.014 inch.

6. The device of claim 1 wherein the distal end of the shaft is tapered.

7. The device of claim 6 wherein the tapered distal end has a maximum diameter of about 0.014 inch, a minimum diameter of about 0.003 inch, and a length of about 15 cm.

8. The device of claim 1 wherein the helical coil is made of wire.

9. The device of claim 8 wherein the wire is formed of a material selected from the group consisting of stainless steel, platinum, Nitinol, MP35N, and palladium.

10. The device of claim 8 wherein the wire has a diameter of about 0.004 inch.

11. The device of claim 1 wherein the outer diameter of the helical coil is about 0.018 inch.

12. The device of claim 1 wherein the length of the helical coil is in the range between about 2 and 10 cm.

13. The device of claim 12 wherein the length of the helical coil is about 5 cm.

14. The device of claim 1 wherein the first bend and the second bend are nearer to the distal tip than any other bends of the helical coil, and wherein the first bend and the second bend respectively define first and second bend angles that face in the same direction.

15. The device of claim 1 wherein the first bend and the second bend are nearer to the distal tip than any other bends of the helical coil, and wherein from one perspective the first bend is tangent to the longitudinal axis and the second bend is not tangent to the longitudinal axis.

16. The device of claim 1 wherein the loop lies on a two-dimensional geometrical plane, and wherein the first and second bends further orient the two-dimensional geometrical plane at the angle relative to the longitudinal axis.

17. A thrombi removal device comprising:
a shaft including a distal end and a proximal end; and
a helical coil including a proximal coil end attached to the distal end of the shaft, a plurality of spaced apart body portions each having bends forming a helix, and a distal coil end shaped as a loop, the loop having a distal tip that defines a most distal part of the helical coil, wherein first and second bends formed adjacent the loop orient the loop at an angle relative to a longitudinal axis extending through the helical coil such that the distal tip is spaced a distance from the longitudinal axis, at least one body portion having an angle relative to the longitudinal axis that is substantially the same as the angle at which the loop is oriented, the body portions having substantially a same diameter along an entire length of the helical coil.

18. The device of claim 17 wherein the first bend and the second bend are nearer to the distal tip than any other bends of the helical coil, and wherein the first bend and the second bend respectively define first and second bend angles that face in the same direction.

19. The device of claim 17 wherein the first bend and the second bend are nearer to the distal tip than any other bends of the helical coil, and wherein from one perspective the first bend is tangent to the longitudinal axis and the second bend is not tangent to the longitudinal axis.

20. The device of claim 17 wherein the loop lies on a two-dimensional geometrical plane, and wherein the first and second bends further orient the two-dimensional geometrical plane at the angle relative to the longitudinal axis.

* * * * *